United States Patent
Nakanishi

(10) Patent No.: US 7,561,657 B2
(45) Date of Patent: Jul. 14, 2009

(54) X-RAY CT DEVICE

(75) Inventor: Satoru Nakanishi, Utsunomiya (JP)

(73) Assignees: Kabushiki Kaisha Toshiba, Tokyo (JP); Toshiba Medical Systems Corporation, Otawara-shi (JP)

(*) Notice: Subject to any disclaimer, the term of this patent is extended or adjusted under 35 U.S.C. 154(b) by 0 days.

(21) Appl. No.: 12/020,638

(22) Filed: Jan. 28, 2008

(65) Prior Publication Data

US 2008/0212735 A1      Sep. 4, 2008

(30) Foreign Application Priority Data

Jan. 31, 2007      (JP)      ............... 2007-021940

(51) Int. Cl.
*A61B 6/03* (2006.01)
(52) U.S. Cl. ................. 378/4; 378/15; 378/19
(58) Field of Classification Search ........... 378/4, 378/15, 19, 20, 205, 208
See application file for complete search history.

(56) References Cited

U.S. PATENT DOCUMENTS

| | | | |
|---|---|---|---|
| 5,864,597 A * | 1/1999 | Kobayashi | 378/4 |
| 6,418,186 B1 * | 7/2002 | Kawai et al. | 378/19 |
| 7,031,423 B2 * | 4/2006 | Tsukagoshi | 378/4 |
| 7,349,520 B2 * | 3/2008 | Nakashima | 378/4 |
| 2003/0076920 A1 * | 4/2003 | Shinno et al. | 378/4 |
| 2003/0091157 A1 * | 5/2003 | Nakanishi et al. | 378/205 |
| 2006/0067457 A1 | 3/2006 | Zamyatin et al. | |
| 2006/0177002 A1 | 8/2006 | Toth et al. | |
| 2007/0211845 A1 * | 9/2007 | Nishide et al. | 378/4 |

FOREIGN PATENT DOCUMENTS

| | | |
|---|---|---|
| EP | 1 470 782 A2 | 10/2004 |
| EP | 1 712 181 A2 | 10/2006 |
| JP | 2003-153893 | 5/2003 |
| JP | 2004-113271 | 4/2004 |
| JP | 2006-95297 | 4/2006 |
| WO | WO 2004-072905 A1 | 8/2004 |
| WO | WO 2005/004063 A2 | 1/2005 |

OTHER PUBLICATIONS

R. Proksa, et al., "The n-Pl-Method for Helical Cone-Beam CT", IEEE Transactions on Medical Imaging, vol. 19, No. 9, XP002241193, ISSN: 0278-0062, Sep. 1. 2000, pp. 848-863.

* cited by examiner

*Primary Examiner*—Irakli Kiknadze
(74) *Attorney, Agent, or Firm*—Oblon, Spivak, McClelland, Maier & Neustadt, P.C.

(57) ABSTRACT

An X-ray CT device according to the present invention produces an X-ray beam of a cone shape in the direction of the body axis of a subject from an X-ray source, performs a helical scanning operation in accordance with the relative movement and relative rotational motion of the X-ray source and the subject, processes data that is collected by a data collecting unit, and reconstructs an image by back-projecting the processed data at a reconstruction processing unit. When the moving speed of the bed is defined, a system controlling unit determines the optimal collection condition for a two-dimensional array-type X-ray detector.

8 Claims, 5 Drawing Sheets

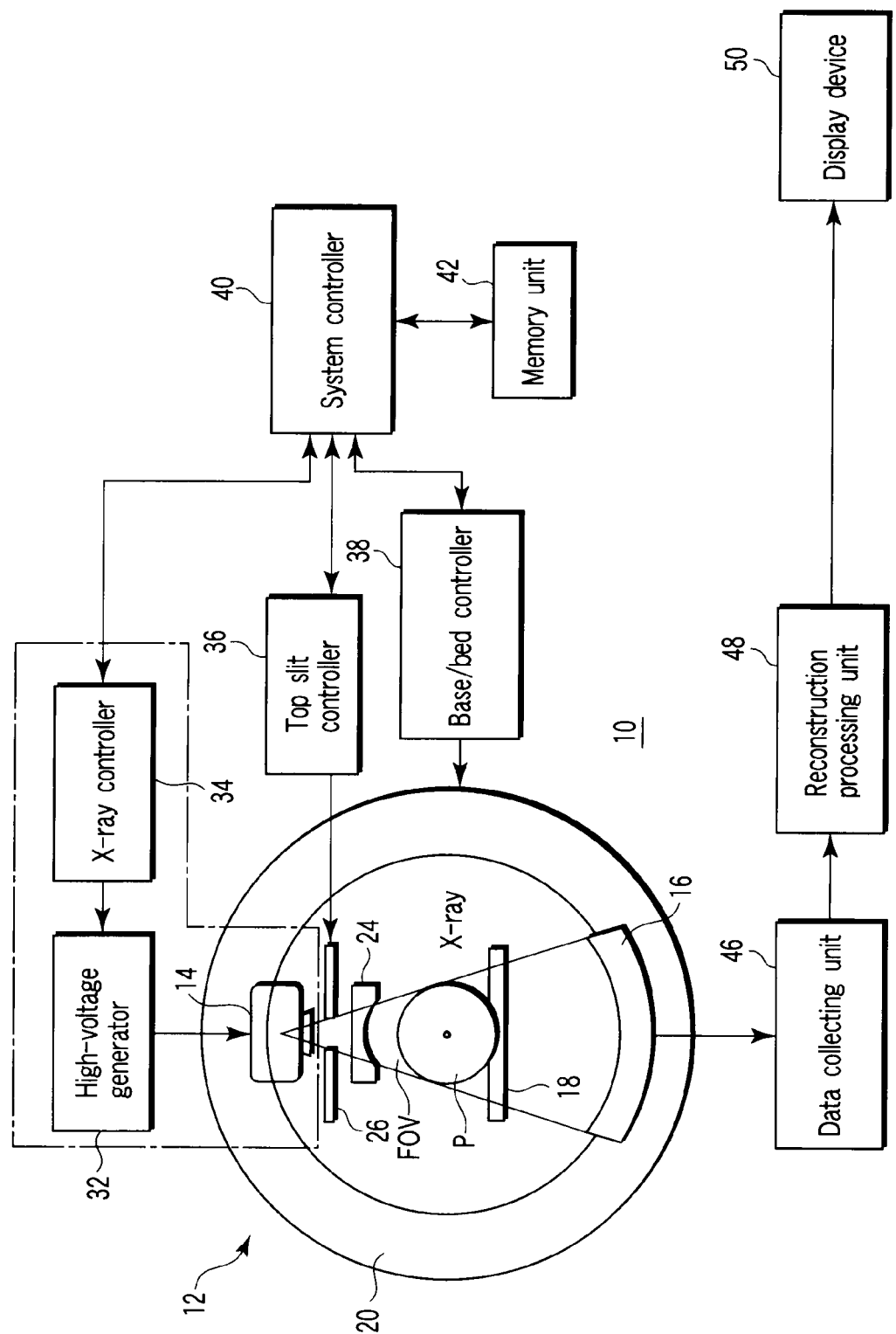
F I G. 1

X-RAY CT DEVICE

CROSS-REFERENCE TO RELATED APPLICATIONS

This application is based upon and claims the benefit of priority from prior Japanese Patent Application No. 2007-021940, filed Jan. 31, 2007, the entire contents of which are incorporated herein by reference.

BACKGROUND OF THE INVENTION

1. Field of the Invention

The present invention pertains to a technology of automatically determining collection conditions for complete-solution cone beam helical reconstruction, and especially to an X-ray CT device for radiating a living body with X-rays and thereby acquiring internal body information as an image.

2. Description of the Related Art

In the field of X-ray CT devices, a system of collecting projection data from various angles with an X-ray tube for producing an X-ray beam and an X-ray detector positioned across a subject from the X-ray tube rotating around the subject is defined as the third-generation CT. The conventional technologies adopt an X-ray beam of a fan shape and a detector of a one-dimensional array type.

Scanning systems can be divided into two types, conventional scanning and helical scanning. In the conventional scanning, the X-ray tube moves around on the same track. On the other hand, the helical scanning is defined as the X-ray source and the detector continuously rotating around a subject while a bed carrying the subject moves along the direction of the body axis in synchronization with the rotation of the X-ray source and the detector. The helical scanning has been given this name because the X-ray tube moves on a helical track when the coordinates of the tube moving along with the subject are considered. The distance between the positions of the X-ray tube that change in the body-axis direction, or in other words the z-axis direction, in one rotation is defined as a helical pitch.

In addition, a CT incorporating a detector of a two-dimensional array type has been known as a third- or fourth-generation CT. This CT is provided with an X-ray tube that generates an X-ray beam of a cone shape spreading in the body axis-direction, unlike an X-ray of a fan shape, and an X-ray detector that is formed by putting, for example, N rows of one-dimensional array detectors together in the z-axis direction so as to arrange detector elements in a matrix. Such a device is called a cone beam CT.

The complete-solution cone beam helical reconstruction proposed by A. Katsevich in University of Central Florida allows for an image quality level without a cone beam artifact. The method of reconstruction is suggested by Jpn. Pat. Appln. KOKAI Publication No. 2006-095297, for example.

The complete-solution helical reconstruction developed by Katsevich having different bed moving speeds, 1PI and 3PI, allows for an image quality level without cone beam artifacts. The speeds 1PI and 3PI represent different bed moving speeds with respect to the width of the detector for detecting X-rays. 1PI is a bed moving speed at which data equivalent to 180 degrees becomes available, while 3PI is a bed moving speed lower than 1PI, at which data equivalent to 540 degrees becomes available.

In general, the user determines the optimal bed moving speed from a target scanning range and the maximum length of a patient's breath holding time. However, in Katsevich's reconstruction system, the bed moving speed is limited only to 1PI and 3PI, and thus the user is not allowed to freely select a bed moving speed. For instance, in the 0.5-mm×64-row data collection on an X-ray detector of a two-dimensional array type, the bed moving speed can be selected only from 17.8 mm/rotation (3PI) and 45.7 mm/rotation (1PI). The reconstruction could be performed at other bed moving speeds, but the data use efficiency is lowered, only unnecessarily exposing the patient to radiation.

BRIEF SUMMARY OF THE INVENTION

In light of the above, the purpose of the present invention is to offer an X-ray CT device that can carry out a complete-solution cone beam helical reconstruction without unnecessary radiation with respect to the bed moving speed.

In other words, the purpose of the present invention is to offer an X-ray CT device comprising an X-ray source for producing an X-ray beam of a cone shape in a direction of a body axis of a subject, an X-ray detecting unit in which a plurality of detecting elements are arranged in rows along the body axis of the subject, and a reconstructing unit for performing a helical scanning operation in accordance with a relative movement and a relative rotational motion of the X-ray source and the subject, processing collected data and reconstructing an image by back-projecting the processed data, the X-ray CT device further comprising:

a setting unit for making a setting of a moving speed of a bed on which the subject is positioned during the helical scanning operation; and a collection condition determining unit for determining either one of the number of collection rows of the X-ray detecting unit and an X-ray narrowing condition, based on the moving speed.

In addition, the present invention offers an X-ray CT device comprising an X-ray source for producing an X-ray beam of a cone shape in a direction of a body axis of a subject, an X-ray detecting unit in which a plurality of detecting elements are arranged in rows along the body axis of the subject, and a reconstructing unit for performing a helical scanning operation in accordance with a relative movement and relative rotational motion of the X-ray source and the subject, processing collected data and reconstructing an image by back-projecting the processed data, the X-ray CT device further comprising:

a setting unit for making a setting of a moving period of a bed on which the subject is positioned during the helical scanning operation; and a collection condition determining unit for determining either one of the number of collection rows of the X-ray detecting unit and an X-ray narrowing condition, based on the moving period.

The present invention offers an X-ray CT device that can carry out a complete-solution cone beam helical reconstruction without unnecessary radiation with respect to the bed moving speed.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the preferred embodiments given below, serve to explain the principles of the invention.

FIG. 1 is a block diagram showing the structure of an X-ray CT device according to an embodiment of the present invention;

DETAILED DESCRIPTION OF THE INVENTION

Preferred embodiments of the present invention will be explained with reference to the attached drawings.

Figure 2:
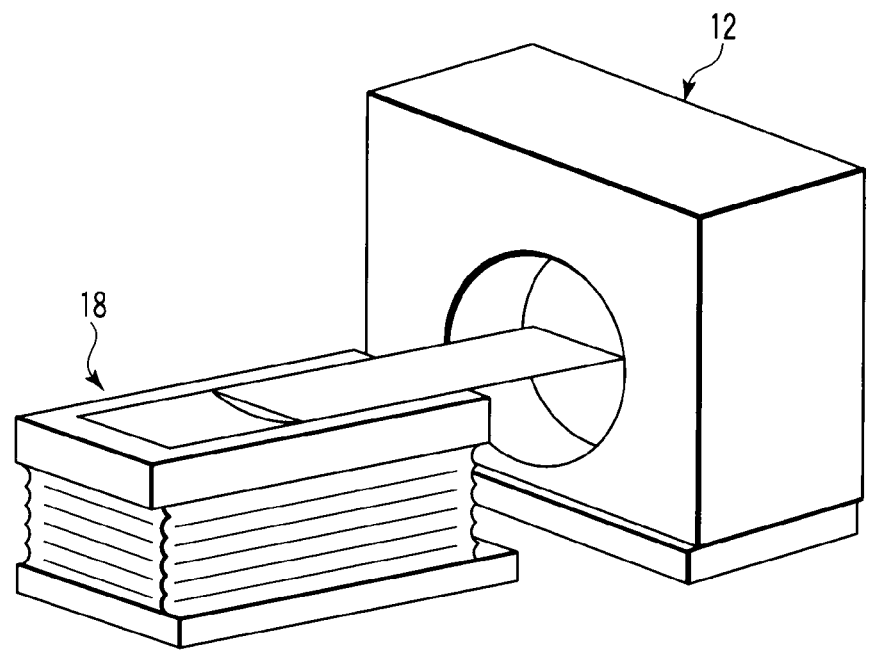
FIG. 2 is a perspective view of the external structure of the gantry illustrated in FIG. 1.
Figure 4:
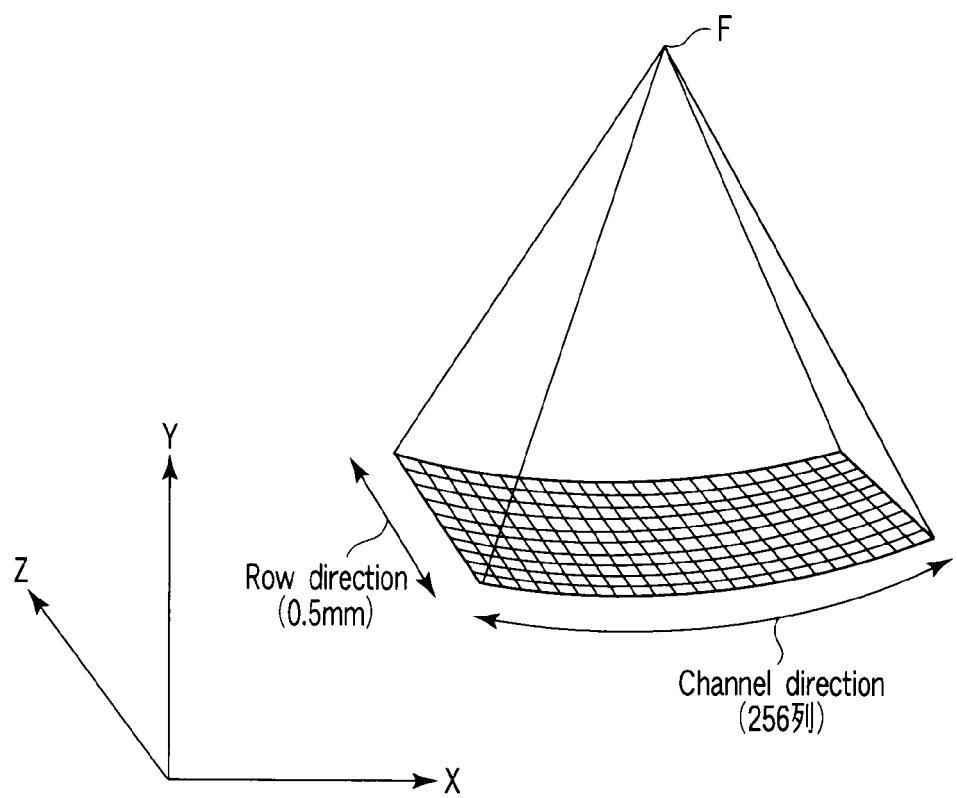
FIG. 4 is a perspective view of the detector of a two-dimensional array type illustrated in FIG. 1.

FIG. 1 is a block diagram showing the structure of an X-ray CT device according to an embodiment of the present invention, while FIG. 2 is a perspective view of the external structure of the gantry illustrated in FIG. 1. FIG. 4 is a perspective view of the detector of a two-dimensional array type illustrated in FIG. 1. The 1PI reconstruction at a high bed moving speed is referred to as "low radiation exposure mode", whereas the 3PI reconstruction at a lower bed moving speed is referred to as "high image quality mode". These modes will be discussed later. At 1PI, an image is reconstructed for a specific slice from projection data equivalent to about 180 degrees. At 3PI, an image is reconstructed for the slice from projection data having a longer collection length (about 540 degrees) than 1PI.

In an X-ray CT device 10, a gantry (also referred to as a base) 12 that serves as a projection data measurement system contains an X-ray source 14 and a two-dimensional array-type X-ray detector 16. The X-ray source 14 produces X-ray cone beams having a shape similar to a cone. The two-dimensional array-type X-ray detector 16 is formed of two-dimensionally arranged detecting elements. The X-ray source 14 and the two-dimensional array-type X-ray detector 16 are arranged on a rotation ring 20 to face each other across a subject P positioned on a sliding top of a bed 18.

In the two-dimensional array-type X-ray detector 16, several one-dimensional array-type detectors, each of which has multiple detecting elements that are one-dimensionally arranged, are stacked together and arranged on the rotation ring 20. It is assumed that one detecting element corresponds to one channel. The X-rays are applied by the X-ray source 14 onto the subject P by way of an X-ray filter 24. The X-rays that have passed through the subject P are detected as an electrical signal by the two-dimensional array-type X-ray detector 16.

An X-ray controller 34 supplies a trigger signal to a high-voltage generator 32. The high-voltage generator 32 applies a high voltage to the X-ray source 14 upon receipt of the trigger signal. This causes the X-ray source 14 to apply the X-rays with the subject P. A top slit 26 is provided in the vicinity of the X-ray source 14 in order to prevent the subject P from being excessively exposed to the radiation. A top slit controller 36 is designed to control the width of the opening of the top slit 26 and is controlled by a system controller 40, which will be described later.

A base/bed controller 38 controls the rotation of the rotation ring 20 of the gantry 12 and the sliding movement of the sliding top of the bed 18 in synchronization with each other. The base/bed controller 38 may control either speeds or periods of the movements. The system controller 40, which serves as the control center of the entire system, controls the X-ray controller 34 and the base/bed controller 38 in such a manner that the X-ray source 14 moves on a spiral track or in other words performs helical scanning when it is seen from the subject P. In particular, in this helical scanning operation, the rotation ring 20 continuously rotates at a certain angular speed and the sliding top moves at a certain speed so that X-rays are emitted from the X-ray source 14 either continuously or intermittently from angles which change at intervals of certain degrees.

A memory unit 42 stores graphs and the like that indicate the relationship between the bed moving speed which will be described later and the number of collection rows of the detector. The stored data is read by the system controller 40.

A signal output by the two-dimensional array-type X-ray detector 16 is amplified for each channel and converted to a digital signal by a data collecting unit 46. The projection data output by the data collecting unit 46 is input into a reconstruction processing unit 48. The reconstruction processing unit 48 acquires back projection data to which an X-ray absorption rate is reflected for each voxel, based on the projection data. In the helical scanning method using X-ray cone beams as incorporated in the present embodiment, the tomography area (the effective field of view) forms a cylindrical shape with a radius of $\omega$ around the rotation axis. The reconstruction processing unit 48 defines voxels (volume elements) in this tomography area and finds the back projection data for each voxel. The three-dimensional image data or tomography data created from the back projection data is sent to a display device 50 and visually displayed as a three-dimensional image or a tomographic image thereon.

Figure 3A:
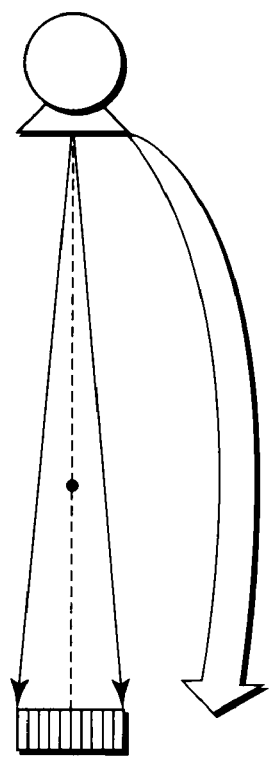
FIGS. 3A and 3B are diagrams for explaining a helical pitch.
Figure 3B:
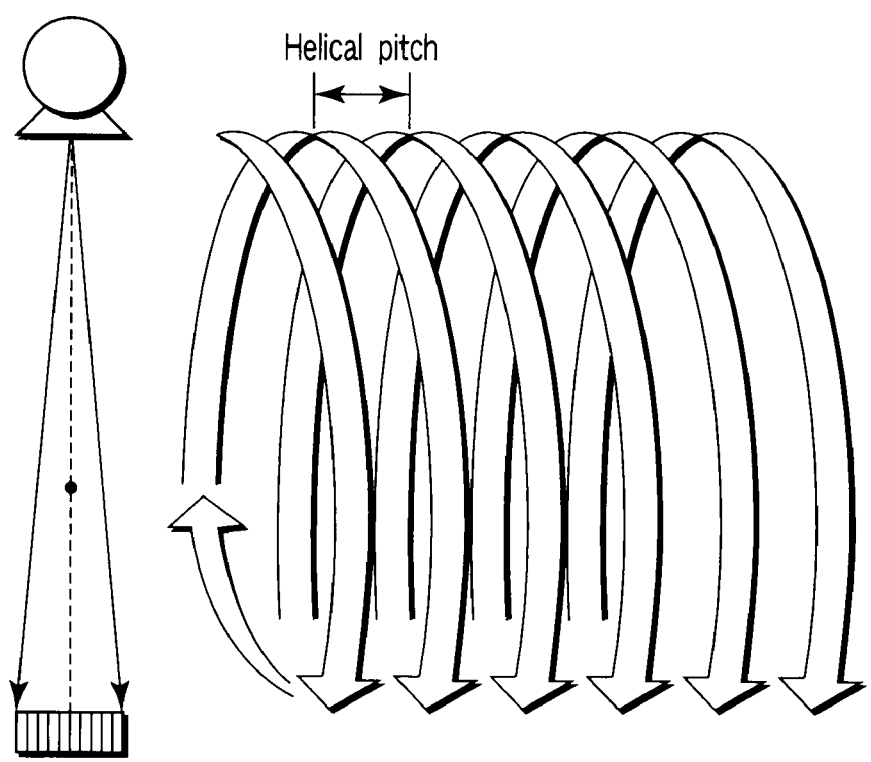

The helical pitch represents the spacing of the spiral track of the X-ray source 14, as illustrated in FIG. 3B. More specifically, the X-ray source 14 rotates 360 degrees along the surface around the center as indicated by an arrow in FIG. 3A. However, the sliding top moves during the 360-degree rotation, and the distance of this movement is defined as a helical pitch.

The 1PI/3PI reconstruction is a typical example of the aforementioned complete-solution cone beam helical reconstruction. The data usage range is determined uniquely from the bed moving speed and the geometry. Conversely, the width of the detector (the collection width×the number of rows) that is necessary for the image reconstruction can be calculated on the basis of the bed moving speed. By collecting the data in accordance with the calculation result (the number of rows), unnecessary exposure to the radiation can be avoided.

According to the present embodiment, as a complete-solution cone beam helical construction (Katsevich reconstruction) of a back projection type utilizing a filter, a structure of calculating the number or rows that is necessary for the optimal 1PI/3PI reconstruction from any bed moving speed designated by the user and collecting data is conceived. In addition, the opening of the top slit is controlled in accordance with the selected number of rows of the detector so that an unnecessary amount of X-ray radiation can be avoided. Hence, the complete-solution cone beam helical reconstruction can be realized without unnecessary radiation exposure with respect to any arbitrary bed moving speed.

Next, the operation of the X-ray CT device according to an embodiment of the present invention will be explained with reference to the flowchart of FIG. 5A.

It is assumed here that the two-dimensional array-type X-ray detector 16 has 256 rows in the channel direction and the width of 0.5 mm in the direction of a row, as illustrated in FIG. 4.

In the flowchart, in step S1, a collection range L is determined in accordance with a scanogram. Then, in step S2, the collection time T is input and determined by the user. In step S3, the bed moving speed CS is calculated on the basis of steps S1 and S2.

In step S4, the number of collection rows of the detector is determined. For instance, a graph indicating the relationship between the bed moving speed (CS) and the number of collection rows (Nseg) as shown in FIG. 6 is stored in advance in the memory unit 42 to explain the relationship between Katsevich reconstruction and the optimal number of rows, and therefore this graph is read from the memory unit 42 to determine the number of collection rows of the detector.

In step S5, the width of the top slit 26 is controlled in accordance with the number of collection rows determined in step S4. In other words, the collection mode is determined. Thereafter, the X-ray source 14 performs a scanning operation in step S6, and the projection data is thereby input to the data collecting unit 46. In step S7, the reconstruction processing unit 48 conducts complete-solution cone beam helical reconstruction on the basis of the projection data obtained in step S6.

In the above flowchart, the bed moving speed CS is calculated from the collection range L and the collection time T determined in steps S1 and S2, but the process is not limited thereto. The bed moving speed CS may be input directly by the user. In step S4, the graph indicating the relationship between the bed moving speed and the number of collection rows is read from the memory unit 42 and referred to in order to determine the number of collection rows of the detector, but the process is not limited thereto. For instance, the determination may be made after the user inputs the aforementioned image mode (high image quality mode/low radiation exposure mode).

Figure 6:
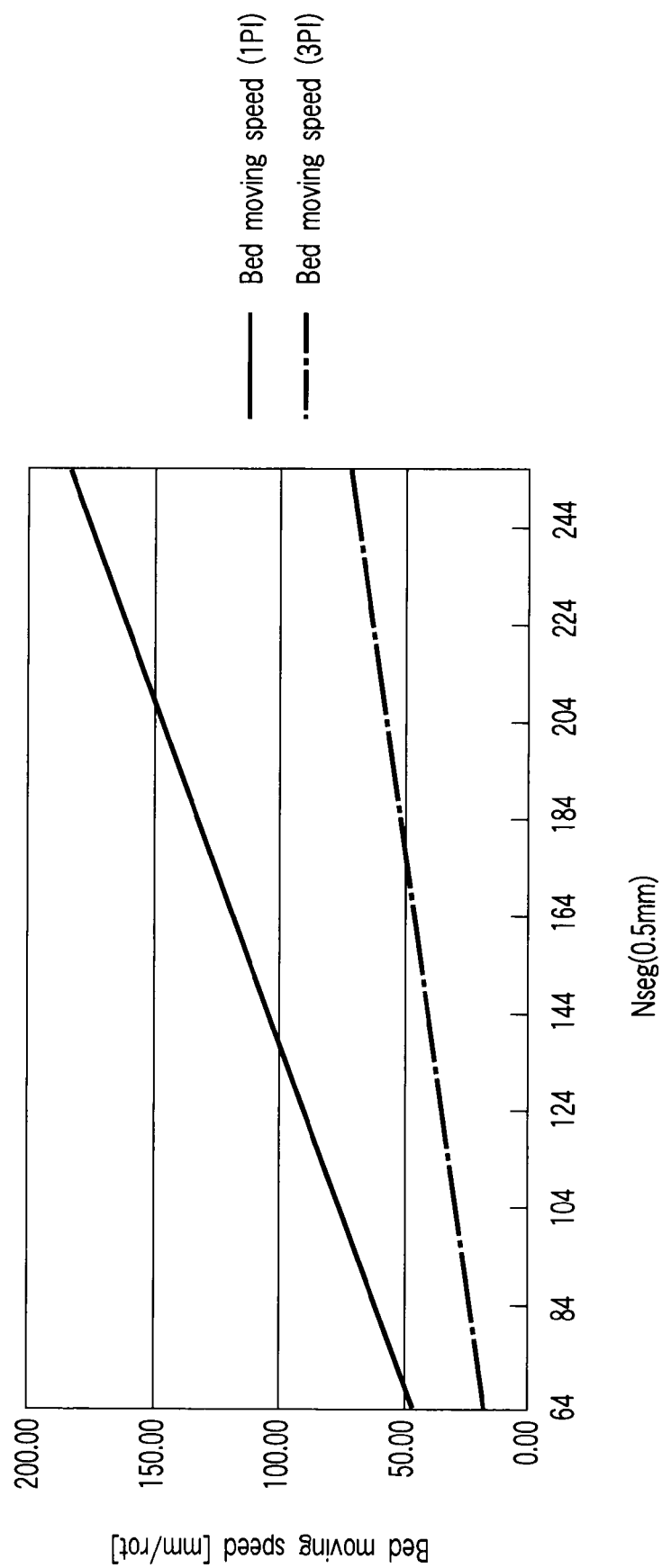
FIG. 6 is a graph showing the relationship between the bed moving speed and the number of collection rows to explain the relationship between Katsevich's reconstruction (1PI/3PI) and the optimal number of rows (at 0.5-mm collection).

When the user desires, for example, to perform data collection at a bed moving speed of 50.0 mm/rotation and image reconstruction in low radiation exposure mode (1PI), the optimal collection condition is determined as 0.5 mm×70 rows according to the graph of FIG. 6 indicating the relationship between Katsevich reconstruction (1PI/3PI) and the optimal number of rows (when collecting at 0.5 mm). When the user desires to perform image reconstruction in high image quality mode (3PI), the optimal collection condition is 0.5 mm×180 rows. Thus, the data collection is performed on the CT device in accordance with this number. When collecting data, the top slit 26 is controlled in accordance with the optimal condition so as to adjust the opening to correspond to the condition of 0.5 mm×70 rows or 0.5 mm×180 rows.

Furthermore, the graph indicating the relationship between the bed moving speed and the number of collection rows of the detector as shown in FIG. 6 may be displayed on the display device 50. In place of the graph, a table may be provided to be referred to, or the condition may be calculated by a mathematical expression.

The above embodiment includes two characteristic curves showing the relationship between the bed moving speed and the number of collection rows of the detector, for 1PI and 3PI. The curves are not limited thereto, however, and any modes, such as 5PI and 7PI, may be adopted as long as an image quality can be maintained without an artifact.

Figure 5A:
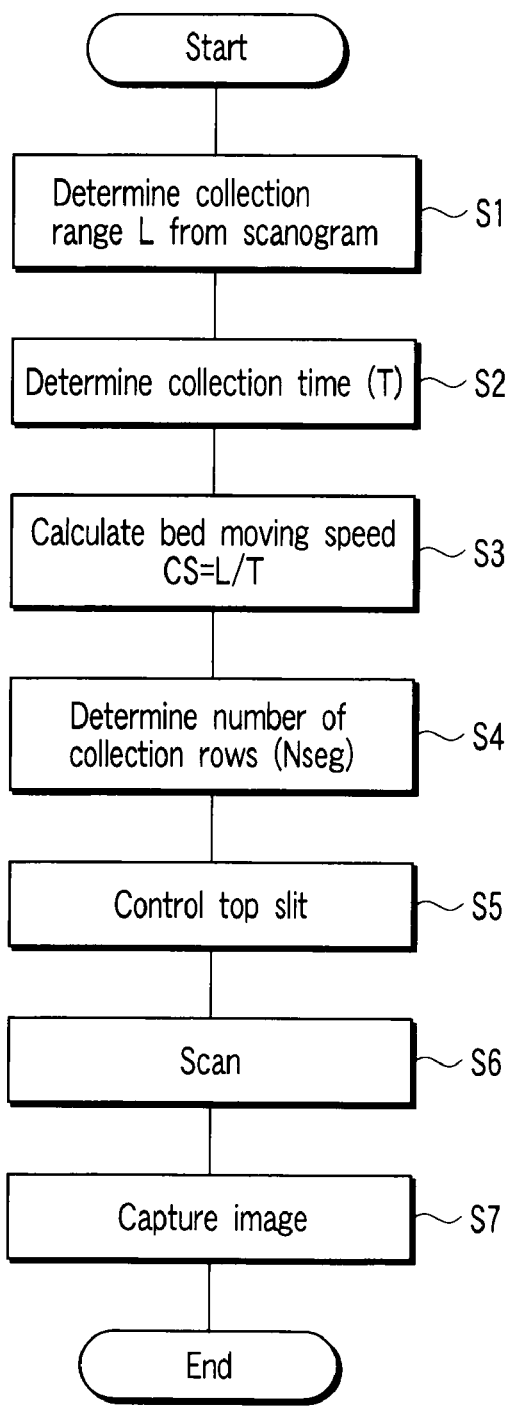
FIG. 5A is a flowchart of the operation of an X-ray CT device according to an embodiment of the present invention.

Moreover, the number of collection rows of the detector is figured out by calculating the bed moving speed as indicated by the flowchart of FIG. 5A according to the above embodiment, but the process is not limited thereto.

Figure 5B:
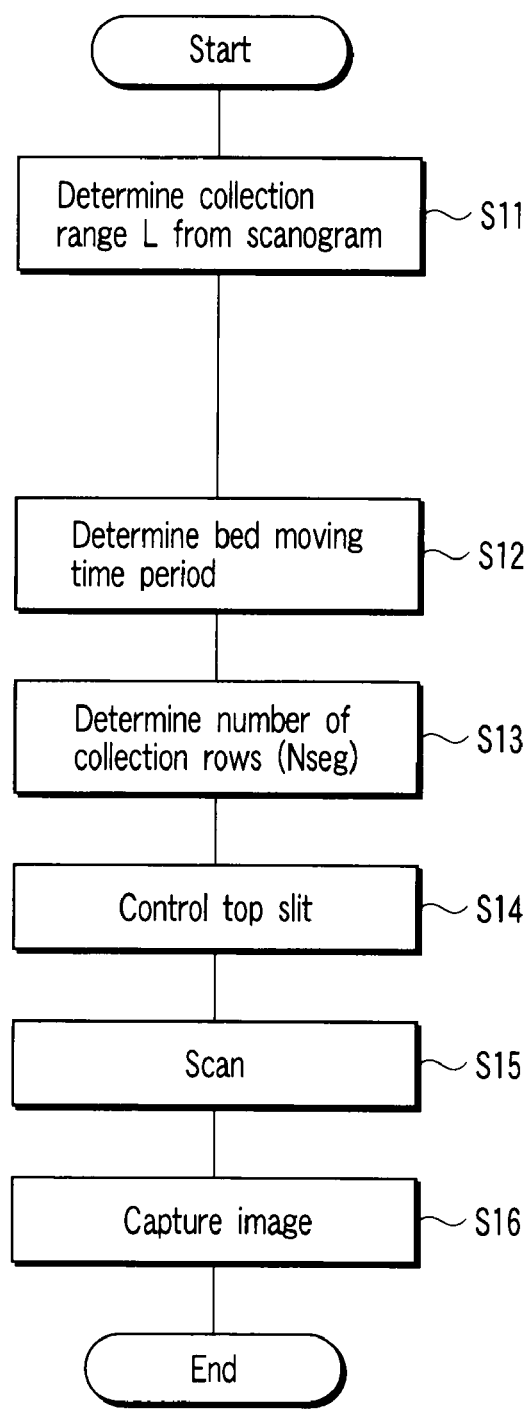
FIG. 5B is a flowchart of another operation of the X-ray CT device according to an embodiment of the present invention.

For instance, the process may be conducted in accordance with the flowchart of FIG. 5B. More specifically, after a collection range L is determined in accordance with a scanogram in step S11, the bed moving period is determined by the user in step S12. Then, the number of collection rows is determined in step S13. The subsequent processing operations in steps S14 through S16 are the same as steps S5 through S7 of FIG. 5A, and thus the explanation is omitted.

As described above, the number of collection rows of the detector may be calculated on the basis of the bed moving speed.

It should be noted that the present invention is not limited to the embodiments explained above, and that various modifications may be added without departing from the scope of the present invention.

Furthermore, the above embodiments include different steps of the invention, and thus various inventions can be attained from suitable combinations of disclosed structural elements. As long as the problems mentioned in the Brief Summary of the Invention can be solved and the aforementioned advantages can be attained, the structure may be presented as an invention even if, for instance, some of the structural elements described in the embodiments are omitted or some of the structural elements are combined together.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray CT device comprising an X-ray source for producing an X-ray beam of a cone shape in a direction of a body axis of a subject, an X-ray detecting unit in which a plurality of detecting elements are arranged in rows along the body axis of the subject, and a reconstructing unit for performing a helical scanning operation in accordance with a relative movement and a relative rotational motion of the X-ray source and the subject, processing collected data and reconstructing an image by back-projecting the processed data, the X-ray CT device further comprising:
   a setting unit for making a setting of a moving speed of a bed on which the subject is positioned during the helical scanning operation; and
   a collection condition determining unit for determining either one of the number of collection rows of the X-ray detecting unit and an X-ray narrowing condition, based on the moving speed.

2. The X-ray CT device according to claim 1, further comprising:
   a memory unit for storing either one of a table and a mathematical expression indicating a relationship between the moving speed of the bed and the number of rows of the detecting elements of the X-ray detecting unit that are to be used.

3. The X-ray CT device according to claim 1, further comprising:
   a calculating unit for calculating the X-ray narrowing condition when the moving speed is set for the bed.

4. The X-ray CT device according to claim 3, further comprising:
 a memory unit for storing either one of a table and a mathematical expression indicating a relationship between the moving speed of the bed and the X-ray narrowing condition.

5. The X-ray CT device according to claim 2 or 4, wherein:
 the memory unit stores either one of the table and the mathematical expression that correspond to 1PI reconstruction and 3PI reconstruction according to Katsevich reconstruction.

6. The X-ray CT device according to claim 1, wherein:
 the collection condition determining unit determines either one of the number of collection rows of the X-ray detecting unit and the X-ray narrowing condition based on a reconstruction condition.

7. The X-ray CT device according to claim 1, further comprising:
 a reconstruction condition setting unit for selecting at least either one of 1PI reconstruction and 3PI reconstruction according to Katsevich reconstruction,
 wherein the collection condition determining unit determines either one of the number of collection rows of the X-ray detecting unit and the X-ray narrowing condition based on the reconstruction condition set by the reconstruction condition setting unit.

8. An X-ray CT device comprising an X-ray source that produces an X-ray beam of a cone shape in a direction of a body axis of a subject, an X-ray detecting unit in which a plurality of detecting elements are arranged in rows along the body axis of the subject, and a reconstructing unit that performs a helical scanning operation in accordance with a relative movement and relative rotational motion of the X-ray source and the subject, processes collected data and reconstructs an image by back-projecting the processed data, the X-ray CT device further comprising:
 a setting unit for making a setting of a moving period of a bed on which the subject is positioned during the helical scanning operation; and
 a collection condition determining unit for determining either one of the number of collection rows of the X-ray detecting unit and an X-ray narrowing condition, based on the moving period.

\* \* \* \* \*